United States Patent [19]

Fekete et al.

[11] Patent Number: 5,543,155
[45] Date of Patent: Aug. 6, 1996

[54] DIFFUSION-OSMOTIC CONTROLLED DRUG-RELEASE PHARMACEUTICAL COMPOSITION AND PROCESS FOR PREPARING SAME

[75] Inventors: Pál Fekete; Mária Király née Ignácz; Gábor Sipos; Zsuzsanna Jámbor née Hoffmann; György Újfalussy; Magdolna Góra née Hernyes; Imre Klebovich; Sándor Drabant; Attila Mándi; Gizella Kiss née Szabó; Erzsébet Bárczay; Mária Krisztián, all of Budapest, Hungary

[73] Assignee: Egis Gyogyszergyar Rt., Budapest, Hungary

[21] Appl. No.: 341,209

[22] Filed: Dec. 5, 1994

[30] Foreign Application Priority Data

Dec. 9, 1993 [HU] Hungary ................. P9303504

[51] Int. Cl.$^6$ ................. A61K 9/24; A61K 9/32
[52] U.S. Cl. ................. 424/473; 424/468; 424/472; 424/482; 514/772.3; 514/781; 514/960
[58] Field of Search ................. 424/468, 472, 424/473, 482

[56] References Cited

U.S. PATENT DOCUMENTS

5,178,866  1/1993  Wright et al. ................. 424/473
5,271,946  12/1993  Hettche ................. 424/490

*Primary Examiner*—Thurman K. Page
*Assistant Examiner*—James M. Spear
*Attorney, Agent, or Firm*—Beveridge, DeGrandi, Weilacher & Young, L.L.P.

[57] ABSTRACT

The invention relates to a novel diffusion-osmotic controlled drug-release pharmaceutical composition containing a one-layer tablet core including a polymeric film-coat, a therapeutically active agent and a hydrophilic polymer; if desired, a two-layer tablet core including active agent and hydrophilic polymer in the first layer thereof and a hydrophilic polymer in the second layer thereof; at least one bore on the part of film-coat in contact with the core or core layer containing the active agent; and, if desired, containing one or more bore(s) in the part thereof in contact with the second layer containing the hydrophilic polymer, which comprises an ammonium methacrylate copolymer as coating material and hydroxypropyl-methylcellulose as hydrophilic polymer. The composition according to the invention is useful for preparing controlled drug-release tablets containing as active agents e.g. β-adrenergic inhibitors (e.g. propranolol) calcium-antagonists (e.g. nifedipine), angiotensin convertase enzyme (ACE) inhibitors (e.g. captopril); prazosin; or nitroglycerol, all used in heart and circulation diseases; vasodilatory active agents (e.g. pentoxyfylline), nonsteroidal antiinflammatory agents (e.g. naproxene), analgetic drugs (e.g. morphine) and drugs acting on the central nervous system (e.g. amitriptyline, buspiron). The invention furthermore relates to a process for the preparation of the above compositions.

51 Claims, 6 Drawing Sheets

DIFFUSION-OSMOTIC CONTROLLED DRUG-RELEASE PHARMACEUTICAL COMPOSITION AND PROCESS FOR PREPARING SAME

The invention relates to novel diffusion-osmotic controlled drug-release pharmaceutical compositions. More particularly, the subject of the invention is an one-layer or two-layer tablet superficially coated with ammonium methacrylate copolymer film and containing polymer(s) dissolving in aqueous media, from which the active agent is released partly by molecular diffusion through the ammonium methacrylate copolymer wall, partly by pressing out through the hole(s) bored on the coat together with the aqueous dispersion or solution of the polymer(s). The invention furthermore relates to a process for the preparation of the above compositions.

Compositions known in the art are osmotic drug-release systems which became known in the pharmaceutical technology in the past decades. Osmotic compositions prepared according to the first patent specifications (U.S. Pat. Nos. 3,845,770 and 3,916,899) consisted of the active agent and a semipermeable coat surrounding it. Being permeable to water, the coat makes possible the penetration of water from the environment into the interior of the composition; however, the coat is impermeable to the active agent and therefore it impedes the molecules of the active agent to get out through the coat into the environment. Thus, the getting-out of the active agent of the composition is provided by one or more hole(s) formed on the coat. During the release of the active agent the composition takes up water from the environment through the coat, then the solution or suspension of the active agent is pressed out into the environment through the opening(s) being present on the coat under effect of the osmotic pressure developing in the system. The rate of water uptake and consequently the rate of active agent release is determined by the permeability to water of the wall; or the potential difference between the osmotic pressure, more precisely the difference between the chemical potential of the solution formed within the composition and that of the environment (the decrease of osmotic pressure through the coat or the extent of difference of chemical potentials), respectively.

However, a composition of this type is useful only for water-soluble active agents or for substances slightly soluble in water when those are employed in a mixture with water-soluble, so-called osmotic additives (auxiliaries). An additional drawback of these compositions lies in that, after cessation of the saturation concentration, the osmotic pressure within the composition decreases and therefore the zero-order, i.e. time-constant rate of active agent release, a great advantage of the composition, is changed.

For eliminating the above drawbacks, a composition has been prepared according to the U.S. Pat. No. 4,111,202, which contains two layers instead of one layer and having osmotic properties within the semipermeable coat. One layer contains the active agent, eventually in a mixture together with an osmotic additive; whereas the other layer, separated from the first layer by an elastic membrane, comprises only osmotic additive. A hole is bored only on the outer semipermeable coat comprising both layers, from the side of the layer containing the active agent. During the release of the active agent, water diffuses into both layers through the semipermeable coat; under effect of development of the osmotic pressure, the pressing-out of solution (or suspension) formed in the layer containing the active agent begins through the opening formed in the wall. This layer is widened towards the elastic membrane under effect of the osmotic pressure of additive dissolving within the layer which contains only osmotic additive and is separated from the first layer by the elastic membrane. While widening, this layer pushes the solution or suspension of the active agent forwards and completely presses it out of the chamber part provided with the opening.

Although these compositions have completely met the desired purpose, i.e. the assuring of the release of water-insoluble active agents at a steady rate, they proved to be unsuitable for practical use. Namely, the development of an elastic membrane separating the layer of osmotic additive from the layer of active agent and the sticking, respectively of the layer containing the osmotic additive together with the layer comprising the active agent, required complicated technical solutions making the preparation of these compositions highly expensive.

According to U.S. Pat. No. 4,327,725, the technical difficulties discussed above can be eliminated by using high molecular crosslinked substances, so-called hydrophilic polymers swelling by water uptake, instead of low molecular osmotic substances in the osmotic layer containing no active agent. Namely, in this case the polymeric substance swells with a sharp interface under effect of water uptake and, while pushing forwards the aqueous solution or suspension of the layer containing the active agent, presses it out through the opening being present on the coat. Thus, the elastic membrane between the layers containing active agent and that containing no active agent can be omitted by this solution and the two-layer tablet can be prepared on industrial scale by using layer-tabletting equipments known and employed for several decades in tabletting technology. Subsequently, the two-layer tablets are provided with a semipermeable coat, usually by employing solutions of cellulose esters in methylene chloride/methanol in a manner known from earlier patent specifications and then a hole of proper size is bored on the coat, in the layer containing the active agent.

In practice, however, this solution also proved to be unsuitable since in the cases of semipermeable coats used the hydrogels employed were unable to resorb sufficient amount of liquid at an appropriate rate through the coat to swell to such an extent which is required for the complete pressing-out of the aqueous solution or suspension of the active agent being in the other layer through the opening formed on the coat. In order to solve the above problem an osmotic composition was developed wherein the layer containing no active agent comprises also a low molecular osmotic substance in addition to the swelling polymer. Thus, the osmotic pressure of this layer is enhanced and the flowing-in of water is accelerated. This osmotic pharmaceutical composition is disclosed in German patent No. 3,417,113 and U.S. Pat. No. 4,612,008.

The composition according to the above patents is a film-coated two-layer tablet, one layer of which contains active agent, low molecular osmotic substance, high molecular osmotic substance and hydrophilic polymer; and the other layer of which incorporates osmotic hydrophilic polymer and low molecular osmotic substance. For assuring the release of the active agent, a hole is bored on the coat from the side of the layer comprising the active agent.

Although the above composition can successfully be used for the preparation of osmotic, prolonged-action compositions, it is burdened by several unpreferable properties, the elimination of which could mean a substantial progress in the preparation of prolonged-action dosage forms.

Such an unadvantageous property of these pharmaceutical compositions lies therein that, beside the hydrophilic polymer, low molecular osmotic substances should also be used in the "placebo" layer for increasing the rate of penetration of water through the semipermeable coat. Conclusively, this leads to an increase in the mass of this layer, and as a final outcome and to an increase in the tablet mass and to an expansion of the physical dimension of the tablet which may be inconvenient on ingestion of the tablet.

Another common drawback of all osmotic compositions known in the art appears in that the semipermeable coat is prepared from a solution of the coating material in an organic solvent, namely methylene chloride/methanol. The reason for this lies in that the inventors enumerate many polymers which could be useful to develop the semipermeable coat, however, various cellulose esters are only used in practice for dissolving which the use of chlorinated solvents is indispensable according to the knowledge in the art.

Thus, for the preparation of osmotic compositions known in the art, chlorinated solvents are employed which are dangerous to an increased degree both to health and to the environment. Although the harmful effects of these can be eliminated by maintaining the appropriate technical measures (laminar-flow work-places, recovery of the solvents), this is accompanied by a considerable increase in the production costs.

An additional drawback of two-layer osmotic compositions is that the layer containing the active agent should be bored out. If the so-called "placebo" layer is bored through, the active agent is of course not released; whereas on boring both layers of the tablet the placebo layer is also pressed out in an aqueous medium; therefore, the tablet essentially behaves as a "simple" osmotic system which cannot provide the complete pressing-out of the layer containing the active agent. For this reason, such a technical solution of the preparation of two-layer tablets known in the art has also to be used which distinguishes the two parts (halves) of tablet before the boring and insures that the coat covering the tablet part incorporating the active agent is only bored through. Thus, an important progress in manufacturing of the composition would be by developing a composition wherein, by boring out both tablet parts, the layer containing the active agent is only pressed out from the tablet because of the peculiar property of the "osmotic" pressing-out layer. The boring-out on both tablet parts is easy to carry out by suitably directing the way of light in boring systems using a laser ray.

Thus, a person skilled in the art of preparing sustained drug-release compositions would consider it to be a very important progress to abandon the osmotic additives from beside the osmotic polymer in osmotic drug-release systems or to eliminate the use of organic solvents e.g. chlorinated solvents during formation of the coats; as well as to provide that, by boring out both parts of the two-layer tablet, the pressing-out proceeds only from the layer containing the active agent.

According to the present invention there is provided a diffusion-osmotic controlled drug-release pharmaceutical composition containing a one-layer tablet core including a polymeric film-coat, a therapeutically active agent and a hydrophilic polymer, if desired, a two-layer tablet core including active agent and hydrophilic polymer in the first layer thereof and a hydrophilic polymer in the second layer thereof, at least one bore on the part of film-coat in contact with the core or core layer containing the active agent, and, if desired, containing one or more bore(s) in the part thereof in contact with the second layer containing the hydrophilic polymer, which comprises an ammonium methacrylate copolymer as coating material and hydroxypropyl-methylcellulose as hydrophilic polymer.

The present invention is based on the recognition that the combination of the diffusion effect with the osmotic effect provides excellent results.

During our work aimed to eliminate the above problems it has surprisiginly been found that all of the three tasks can be solved by preparing a simultaneously diffusive and osmotic drug-release composition instead of an only osmotic drug-release composition. Thus, ammonium methacrylate copolymers, till now used as coating materials of diffusion-controlled pharmaceutical compositions according to the known art, are employed for coating the tablets whereas hydroxypropyl-methylcellulose is employed as hydrophilic swelling material. In this way the release of active agent from the composition by diffusion is insured on the one hand; and on the other hand, hole(s) is (are) bored on the coat and it is provided thereby that in the interior of the composition the solution or suspension of the active agent is released from the composition also by pressing-out through the hole(s) under the pressure developing due to the swelling of hydroxypropyl methylcellulose.

Ammonium methacrylate copolymers used in the coating of the new-type diffusion-osmotic drug release compositions are employed since the middle of the Fifties in the pharmaceutical industry. For the preparation of prolonged-action compositions such copolymers are chiefly employed which are completely insoluble in water but all permeable to various extent and provide thereby the diffusion of molecules of the active agent.

Such copolymers are listed hereinafter.

Ammonium methacrylate copolymer RL (Eudragit RL)
(Ammonio Methacrylate Copolymer, Type A—USP/NF)
(Aminoalkyl Methacrylate Copolymer RL—JSP I)
(Ethyl acrylate)-(methyl methacrylate)-(trimethylammonio)-ethylmethacrylate](1:2:0.2) copolymer, molecular weight 150,000.

Commercially available products (Röhm Pharma, Weiterstadt):

Eudragit RS 100: solid polymer

Eudragit RL 12.5: 12.5% solution in solvent

Eudragit RL 30 D: 30% aqueous dispersion

Ammonium methacrylate copolymer RS (Eudragit RS)
(Ammonio Methacrylate Copolymer, Type B—USP/NF)
(Aminoalkyl Methacrylate Copolymer RS—JSP I)
(Ethyl acrylate)-(methyl methacrylate)-[(trimethylammonio)ethyl methacrylate (1:2:0.1) copolymer, molecular weight 150,000.

Commercially available products:

Eudragit RS 100: solid copolymer

Eudragit RS 12.5: 12.5% solution in solvent

Eudragit RS 30 D: 30% aqueous dispersion

Films prepared from ammonium methacrylate RL/RS copolymers are insoluble in water and digestive juices but swell and are permeable to the dissolved substances. This means that, when used according to the known art, the release of the active agent proceeds by diffusion through these films. The sign RL means the property that the film is easily permeable; whereas the sign RS indicates a difficultly permeable film. Between pH 2 and pH 8 the quaternary ammonium groups of the copolymers are fully dissociated; thus, the permeability of the films is independent of the pH-value and can be controlled by varying the mixing ratio of the two polymers. The manufacturer indicates the field of utilization of Eudragit RL/RS copolymers as follows:

coating of skeletal tablets for regulating the initial profile of release;

coating of pellets, granulates (granular products), crystals;

preparation of granulates or pellets

Röhm Pharma GmbH, Weiterstadt, Prospect (Info RL/RSD-1)

Thus, the usability of ammonium methacrylate copolymers has till now been known only for the production of diffusion-controlled, prolonged-action dosage forms; their utilization for preparing diffusion-osmotic drug-release compositions has neither been disclosed in or suggested by the prior art.

groups) to methyl (Me) groups or in the viscosity of their aqueous solutions, i.e. essentially in the molecular weights of the polymers. The quality demands of various HPMC sorts useful for the preparation of pharmaceutical compositions have been described in more detail in the prescriptions of the United States Pharmacopoea. The connection between the trade names, pharmacopoeal names and characteristic parameters of various HPMC sorts are summarized in Table 1. At present, HPMC sorts are out in circulation by the American DOW Chemical Co. under the trade name Methocel; and by the Japanese Shin-Etsu Chemical Co. under the trade name Metolose.

TABLE 1

Relations between the names and quality parameters of HPMC polymers

| Name of HPMC | | | Methoxy content % | Hydroxy-propoxy content % | Viscosity of a 2% solution (cP) |
| --- | --- | --- | --- | --- | --- |
| USP HPMC | DOW Chem. Methocel | Shin-Etsu Metolose | | | |
| 2910 | E 4M | 60SH-4000 | 29 | 10 | 4000 |
| 2906 | F 4M | 65SH-4000 | 29 | 6 | 4000 |
| 2208 | K 4M | 90SH-4000 | 22 | 8 | 4000 |

Another indispensable component of the novel drug-release system according to the invention is hydroxypropyl-methylcellulose (HPMC). By using HPMC in tablets coated with ammonium methacrylate copolymer film beside the active agent and in the "osmotic" pressing-out layer, the uptake of water through the coat and the swelling pressure or osmotic pressure, respectively, developing within the tablets are capable of providing the release of active agent at an appropriate rate both by diffusion through the film as well as by pressing out through the opening bored in the coat. Namely, as known in the art, ammonium methacrylate copolymer films are permeable to the active agent and other low molecular additives (e.g. sodium and potassium chloride, lactose, mannitol or the like), i.e. the so-called osmotic substances, in addition to water. By using these substances together with active agent in the tablets, the osmotic pressure required to release the active agent cannot be insured in the interior of the tablet since these low molecular osmotic additives rapidly diffuse out through the coat.

Simultaneously, the ammonium methacrylate copolymer films, being permeable to small molecules, are impermeable to the high molecular HPMC-s. Thus, their swelling pressure or osmotic pressure, respectively, is decreased only by their discharge through the hole bored on the coat; on the other hand, due to the high gel strength of HPMC polymers, there can be achieved by using these polymers alone or only in a concentration higher than 30% by weight in the "osmotic" pressing-out tablet part that the material of the pressing out layer is not pressed out of the tablet in spite of boring out both tablet parts.

HPMC polymers useful for the pharmaceutical compositions according to the invention are used for the preparation of pharmaceutical compositions since the Sixties. According to the known art, these hydrophilic polymers are used for increasing the viscosity of aqueous solutions or suspensions, for preparing hydrophilic skeletal tablets and matrixes, furthermore as binders of traditional tablets and for coating film tablets.

The commercially available HPMC polymers differ from each other in the ratio of hydroxypropyl groups (HPr The rate of hydratation of the polymer is directly proportional and the gel strength of the polymer is inversely proportional to the ratio of hydroxypropyl groups introduced to the free hydroxyl groups of the polysaccharide chain of cellulose. Of course, the gel strength is in direct proportion also to the molecular weight of the polymer and the value of viscosity measured in 2% aqueous solution. The viscosity of commercially available HPMC polymers with the lowest molecular weight is 5 cP (named Methocel E5) and 3 cP (named Metolose 60SH-3), respectively, whereas HPMC polymers having the highest molecular weight are Methocel K100M (with a viscosity of 100,000 cP) and Metolose 60SH 4000, 65SH 4000 and 90SH 4000 (having a viscosity of 4000 cP each).

In the prolonged-action compositions according to the invention any of HPMC polymers can be used in the one-layer tablets or in the layer containing the active agent of two-layer tablets; whereas the higher molecular weight HPMC polymers having a viscosity higher than 1000 cP in 2% aqueous solution are only suitable in the "osmotic" pressing out layer of two-layer tablets.

The rate of drug release from the pharmaceutical composition according to the invention is determined by two factors: the diffusion of active agent through the tablet coat and its pressing-out in the form of a solution or suspension which proceeds through the hole bored on the coat under the effect of differential osmotic pressure. The drug-release from the tablets becomes steady after a transitional non-steady state, when water molecules diffuse through the coat into the interior of the tablet, dissolve the active agent, furthermore swell and dissolve the HPMC. In this steady state, the rate of drug-release can be described by the following correlations.

In the case of one-layer tablet
Drug-release by diffusion:

$$dm_D/dt = A \cdot C_i \cdot k_D / h$$

wherein $dm_D/dt$ means the rate of drug-release by diffusion ($MT^{-1}$)

A is the surface of tablet ($L^2$)

$C_t$ is the saturation concentration of the active agent ($M/L^3$)

$k_D$ means the rate constant of diffusion of the active agent ($ML^{-2}T^{-1}$)

h is the thickness of coat (L) „

M,L,T are the dimensions of weight, length and time

Osmotic drug-release:

$$dm_o/dt = dV/dt * C = A * C * \Delta\pi * k_v/h$$

wherein $dm_o/dt$ means the rate of osmotic drug-release ($MT^{-1}$)

dv/dt means the rate of water diffusion into the tablet ($MT^{-1}$)

C is the active agent concentration of the liquid being present in the tablet ($ML^{-3}$)

$\Delta\pi$ means the osmotic pressure drop through the tablet coat ($ML^{-1}T^{-2}$)

kv is the rate coefficient of diffusion of the water ($ML^{-2}T^{-1}$)

The total rate of drug-release from the composition is defined by the sum of drug-release by diffusion plus drug-release by osmosis:

$$dm/dt = (k_D * A * C_t + k_v * A * \pi * C)/h$$

or, since $C_t = C$, when the active agent dissolves in the water diffusing through the film coat and therefore:

$$dm/dt = (k_D + k_v * \Delta\pi) A * C/h$$

wherein dm/dt is the total rate of drug-release from the tablet ($MT^{-1}$).

In the case of two-layer tablet

Drug-release by diffusion:

$$dm_D/dt = A_A * C_t * k_D/h$$

wherein $A_A$ means the surface of tablet part containing the active agent ($L^2$)

Osmotic drug release:

$$dm_o/dt = (dV_A/dt + dV_P/dt) * C = (A_A * \Delta\pi_A + A_P * \Delta\pi P) * C * k_v/h$$

wherein $dV_A/dt$ means the rate of diffusion of water into the tablet part containing the active agent ($MT^{-1}$)

$DV_P/dt$ means the rate of water diffusion into the placebo tablet part ($MT^{-1}$)

$A_P$ is the surface of placebo tablet part ($L^2$)

$\pi_A$ means the osmotic pressure drop through the coat of tablet part containing the active agent ($ML^{-1}T^{-2}$)

$\pi_P$ is the osmotic pressure drop through the coat of placebo part ($ML^{-1}T^{-2}$)

The total rate of drug-release from a two-layer tablet is defined by the sum of drug-release by diffusion plus drug-release by osmosis:

$$dm/dt = A_A * C_t * k_D/h + (A_A * \Delta\pi_A + A_P * \Delta\pi_P) * C * k_v/h$$

Thus, the drug-release from the tablets according to the invention occurs by molecular diffusion through the intact coat depending on the diffusivity of the active agent through the polyacrylate film and by the driving force of osmotic and polymer-swelling pressure developing in the tablet interior through the hole bored on the tablet coat. The ratio of the two ways of drug-release is defined by diffusivity of the active agent through the ammonium polyacrylate polymer film. In the case e.g. of active agents well-soluble in water (such as salbutamol, metoprolol, bricanyl or the like), the concentration of solution formed within the tablet provides a significant drug-release by diffusion. The rate of drug-release of such active agents is defined by the totality of diffusion and polymer-swelling processes. Contrary to this, in the case of active agents slightly soluble in water (such as nifedipine), the drug-release by diffusion is low due to the low value of active agent concentration developing in the tablet interior; thus, the extent of drug release from the composition is defined chiefly by the driving force of pressure arising from the swelling of the polymer.

Thus, the pharmaceutical compositions according to the invention are prepared as follows.

a) One-layer composition

For the preparation of a composition containing one-layer tablet core, the active agent is homogenized with 5 to 30% by weight of HPMC polymer in dry form calculated for the weight of the uncoated tablet core, if desired, together with at most 90% by weight of tabletting filler (tablet-filling material) (such as cellulose, lactose, mannitol, starch, microcrystalline cellulose, calcium phosphate and the like) and, if desired, granulated in a manner known in the practice of tablet preparation. The granulating may be carried out by using any of both the "dry process" or "wet process". In the case of the dry process, the homogenate is mixed with at most 5% by weight of tabletting binding material (e.g. polyvinylpyrrolidone, HPMC, polyvinylbutyral or hydroxypropyl-cellulose and the like), then briquetted or tabletted, ground and sieved to the desired (usually 0.1 to 1.0 mm) size. When wet-granulated, the homogenate is kneaded together with the solution of a binding material (such as polyvinylpyrrolidone, hydroxypropyl-cellulose, methyl-cellulose, gelatine, polyvinyl alcohol or the like) in water or a $C_{1-3}$ alcohol; or the solution of the binder is sprayed onto the fluidized powder mixture in a fluidized-bed granulating equipment. Subsequently, the granulate formed is dried and sieved to the desired size (usually less than 1.0 mm). Then, after adding lubricants (e.g. magnesium stearate, stearic acid, colloidal silicon dioxide, hydrogenated castor oil, talc and the like), the original homogenate or the granulate prepared therefrom is compressed to biconvex-shaped tablets (tablet cores) containing the desired amount of active agent. The tablets are coated with an ammonium methacrylate copolymer film in an amount of 3 to 25 mg/cm² calculated for the surface of tablet cores in a manner known in the practice of film-coating. The coating may be carried out by using the solution of ammonium methacrylate copolymers in ethanol, propanol or acetone or any mixture thereof or, preferably the aqueous latex dispersion of the polymers. The coating may equally be accomplished in a traditional perforated-wall kettle, in a fluidized-bed device or sphere-coating apparatus. Finally, one or more bore(s) of 0.01 to 1 mm² in size is (are) formed on the coat of the tablet obtained in order to insure the osmotic drug-release. The bore(s) may be formed by using a mechanical boring device or a boring equipment using a laser ray.

The quality and quantity of HPMC used for the preparation of tablets, the quality of ammonium methacrylate copolymer used for coating the tablets, the amount of coat as well as the diameter of the bore to be formed can be determined by a person skilled in the art, in the knowledge of the dissolution demands relating to the active agent given, by carrying out a few experiments on the basis of recognitions described in the present invention.

BRIEF DESCRIPTION OF THE DRAWINGS

The cross-section of the composition after production is shown in FIG. 1; whereas the steady state of drug-release after ingestion is illustrated in FIG. 2. As shown in FIG. 2, the ammonium methacrylate film-coat swelling under influence of water develops a nearly spheric-symmetrical shape on account of the swelling pressure of HPMC polymer being present in the tablet.

The reference numbers used in the Figures are as follows:
For FIGS. 1 and 2
- 10 Diffusion-osmotic drug-release pharmaceutical composition
- 11 Ammonium methacrylate copolymer coat
- 12 Tablet containing active agent and HPMC
- 13 Opening bored on the coat
- b) Two-layer tablet The homogenate or, if desired, the granulate for preparing the layer containing the active agent of two-layer tablets are produced as described for the preparation of one-layer tablets. For preparing the other layer of the tablet containing no active agent, a homogenate is prepared from a 2% solution of HPMC having a viscosity higher than 1000 cP alone or together with 0 to 70% by weight of tabletting filler (such as e.g. cellulose, microcrystalline cellulose, lactose, mannitol, dicalcium phosphate and the like), which, if desired, are then granulated in way known in the practice of tabletting, by using any of the processes described above. Subsequently, two-layer tablets containing the required amount of active agent in one layer and the required amount of HPMC in the other one, are prepared from the powder mixture of two kinds or, if desired, from the granulates prepared therefrom, which the lubricants needed had separately been mixed to by applying the second tablet core layer to the first one. These operations are carried out in a manner known in the practice of tabletting. For establishing the film-coating, the tablets are preferably biconvex-shaped. Then, the tablets are coated with an ammonium methacrylate copolymer film in an amount of 3 to 25 mg/cm$^2$ calculated for the surface of the two-layer tablet cores. The coating may be carried out by using a solution of the ammonium methacrylate copolymer in ethanol, propanol or acetone or a mixture thereof or preferably, by employing an aqueous latex dispersion of the copolymer. (Several instructions relating to the coating process have been published in the booklets of the Röhm Pharma Company, the manufacturer of the Eudragit sorts.) Finally, bore(s) of 0.1 to 1.0 mm$^2$ in size should be formed on the coat of the tablet prepared in order to provide the osmotic drug-release.

For functioning of the composition it is sufficient to bore one single hole on the coat covering the tablet part containing the active agent, though the functioning of the composition is not influenced by simultaneously establishing a bore also on the coat covering the other tablet layer containing no active agent. If desired, several bores may be developed on the tablet part containing the active agent or on both tablet parts. The bore(s) may equally be formed by using a mechanical boring device or a boring equipment working with a laser ray.

The quality and quantity of the HPMC types to be employed in the two tablet layers, furthermore the quality of the ammonium methacrylate copolymer to be used in the film coat, and the thickness of coat as well as the size of bore(s) can be determined by a person skilled in the art by carrying out only a few experiments on the basis of the recognitions described in the present invention.

If desired, the tablets prepared in this way, which are useful for therapeutical use in themselves, may be provided with an additional water-soluble coat and with an inscription for the sake of identification.

In the case when it is desired to form a bore only on the tablet part containing the active agent, both tablet parts should be made distinguishable by colouring one or both granulate(s) or using a compressing device with different shapes; furthermore, when different colours are employed, the polyacrylate coat controlling the drug-release has to be transparent to make the individual layers (separate layers) recognizable at boring. When bore(s) is (are) formed on both parts of the tablets, the polyacrylate coat can also be coloured and in this case the colouring of tablets after boring can be eliminated.

The structure of two-layer tablets is illustrated in FIGS. 3 to 6.

New reference numbers on the Figures are as follows.
- 14 Tablet part containing the active agent and HPMC
- 15 Tablet part containing no active agent
- 16 Opening on the coat of tablet part containing the active agent
- 17 Opening on the coat of tablet part containing no active agent.

The composition according to the present invention is useful for the production of prolonged-action tablets with a very wide scope of active agents. Its utilization is limited only by an eventual incompatibility between the active agent and HPMC or ammonium methacrylate copolymers, respectively; or by the case when a single dose required exceeds 1500 mg since the physical size of the composition prepared in this way makes it nearly impossible to ingest it.

The process according to the present invention is particularly preferably useful for the preparation of prolonged-action compositions containing active agents used for the treatment of chronic diseases.

Active agents of this kind are: β-adrenergic inhibitors used in heart and circulation diseases such as e.g. propranolol, i.e. chemically 1-[(1-methylethyl)amino]-3-(1-naphthalenyloxy)-2-propanol; metoprolol, i.e. 1-[4-(2-methoxyethyl)phenoxy]-3-[(1-methylethyl)amino]-2-propanol; oxprenolol, i.e. 1-[(methylethyl)amino]-3-[2-(2-propenyloxy)phenoxy-2-propanol; pindolol, i.e. 1-(1H-indol-4-yloxy)-3-[(methylethyl)amino]-2-propanol; calcium-antagonists, such as e.g. nifedipine, i.e. 1,4-dihydro-2,6-dimethyl-4-(2-nitrophenyl)-3,5-pyridinedicarboxylic acid dimethyl ester; diltiazem, i.e. (2S-cis)-3-(acetyloxy)-5-[2-(dimethylamino)ethyl]-2,3-dihydro-2-(4-methoxyphenyl)-1,5-benzothiazepin-4(5H)-one; verapamil, i.e. α-{3-[[2-(3,4-dimethoxyphenyl)ethyl]methylamino]propyl}-3,4-dimethoxy-α-1-(methylethyl)-benzeneacetonitrile; nicardipine, i.e. 1,4-dihydro-2,6-dimethyl-4-(3-nitrophenyl)-3,5-pyridine dicarboxylic acid methyl-2-[methyl(phenylmethyl)amino]ethylester; nitrendipine, i.e. 1,4-dihydro-2,6-dimethyl-4-(3-nitrophenyl)-3,5-pyridine dicarboxylic acid ethylmethyl ester; felodipine, i.e. 4-(2,3-dichlorophenyl)-1,4-dihydro-2,6-dimethyl-3,5-pyridine-dicarboxylic acid ethylmethyl ester; gallopamil, i.e. α-{3-[[2-(3,4-dimethoxyphenyl)ethyl]methylaminopropyl]-3,4,5-trimethoxy-α-(1-methylethyl)-benzeneacetonitrile; the so-called organic nitrate active agents, such as e.g. isosorbide dinitrate, i.e. 1,4:3,6-dianhydro-D-glucitol-dinitrate; isosorbide 5-mononitrate, i.e. 1,4:3,6-dianhydro-D-glucitol-5-nitrate; nitroglycerol, i.e. 1,2,3-propanetriol-trinitrate; the so-called ACE (angiotensin-convertase enzyme) inhibitors, e.g. captopril, i.e. (S)-1-(3-mercapto-2-methyl-1-oxopropyl)-L-proline; enalapril, i.e. (S)-1-{N-[(ethoxycarbonyl)-3-phenylpropyl]alanyl}-L-proline; the so-called central alpha-agonist active agents, e.g. prazosin, i.e. 1-(4-amino-6,7-dimethoxy-2-quinazolinyl)-4-(2-furanylcarbonyl)piperazin; terazosin, i.e. 1-(4-amino-6,7-dimethoxy-2-quinazolinyl)-4-[(tetrahydro-2-furanyl)carbonyl]piperazine; the so-called lipid-level-lowering active agents, e.g. gemfibrozil, i.e. 5-(2, 5-dimethylphenoxy)-2,2-dimethylpentanonic acid; lovastatin, i e. 1S-[1α(R*),3α,7β,8β(2S*,4S),8α-β]-2-methylbutanoic acid 1,2,3,7,8,8a-hexahydro-3,7-dimethyl-8-[2-tetrahydro-4-hydroxy-6-oxo-2H-pyran-2-yl)ethyl]-1-naphthalenyl ester; the so-called anticoagulant active agents, e.g. ticlopidine, i.e. 5-[(2-chlorophenyl)methyl]-4,5,6,7-tetrahydrothieno[3,2-c]pyridine; the so-called vasodilatory active agents, e.g. pentoxyfylline, i.e. 3,7-dihydro-3,7-dimethyl-1-(5-oxohexyl)-1H-purin-2,6-dione; the so-called antiulcer active agents, e.g. cimetidine, i.e. N-cyano-N"-methyl-N"-{2-[[(5-methyl-1H-imidazol-4-yl)-methyl]thio] ethyl}-guanidine; ranitidine, i.e. N-2-{[[5-[(dimethylamino)methyl]-2-furanyl]methyl]thio]ethyl}-N"-methyl-2-nitro-1,1-ethenediamine; the so-called nonsteroidal antiinflammatory agents, e.g. dichlofenac, i.e. 2-[(2,6-dichlorophenyl)amino]benzeneacetic acid; naproxen, i.e. (S)-6-methoxy-α-methyl-2-naphthaleneacetic acid; sulindac, i.e. (Z)-5-fluoro-2-methyl-1-{[4-methylsulfinyl)phenyl]methylene}-1H-indene-3-acetic acid; the so-called antihistamines, e.g. dimethindene, i.e. N,N-dimethyl-3-[1-(2-pyridinyl)ethyl]-1H-indene-2-ethaneamine; astemizole, i.e. 1-[(4-fluorophenyl)methyl]-N-{1-[2-(4-methoxyphenyl)ethyl]-4-piperidinyl}-1H -benzimidazole-2-amine; terfenadine, i.e. α-[4-(1,1-dimethylethyl)phenyl]-4-(hydroxydiphenylmethyl)-1-piperidine butanol; cetirizine, i.e. {2-[4-[(4-chlorophenyl)phenylmethyl]-1-piperazinyl]ethoxy acetic acid; the so-called anti-asthmatics, e.g. albuterol, i.e. $\alpha^1$-{[(1,1-dimethylethyl)amino]methyl}-4-hydroxy-1,3-benzenedimethanol; terbutaline, i.e. 5-{2-[(1,1-dimethylethyl)amino]-1-hydroxyethyl}-1,3-benzenediol; theophylline, i.e. 3,7-dihydro-1,3-dimethyl-1H-purine-2,6-dione; various analgetic substances, e.g. morphine, i.e. (5α,6α)-7,β-didehydro-4,5-epoxy-17-methylmorphinane-3,6-diol; codeine, i.e. (5α,6α)-7,8-didehydro-4,5-epoxy-3-methoxy-17-methyl-morphinan-6-ol; central nervous system agents, e.g. amitriptyline, i.e. 3-(10,11-dihydro-5H-dibenzo[a,d]cyclohepten-5-ylidene)-N,N-dimethyl-1-propanamine; and buspiron, i.e. 8-[4-[4-(2-pyrimidinyl)-1-piperazinyl]-8-azaspiro[4.5]decane-7,9-dione carbamazepine, i.e. 5H-dibenz[b,f]azepine-5-carboxamide and the like.

The drug-release of compositions according to the present invention can optionally be controlled within an interval from a few hours up to a few days by changing the parameters affecting the rate of release (quality and quantity of HPMC; quality and thickness of the ammonium methacrylate copolymer film size and number of bores). However, on the basis of practical points of view it is suitable to adjust the time of release to a duration of 4 to 24 hours.

The invention is illustrated in detail by the following non-limiting Examples.

Example 1

Round, biconvex-shaped tablets of 8 mm in diameter were prepared which contained 8 mg of salbutamol base (chemically α-{[(1,1-dimethylethyl)amino]methyl}-4-hydroxy-1,3-benzenedimethanol) as active agent; 160 mg of lactose monohydrate as filling material; 6 mg of polyvinylpyrrolidone (Povidon K-90 GAF) as binding material; 20 mg of hydroxypropyl-methylcellulose (Methocel K15M, Colorcon) in 2% aqueous solution with a viscosity of 15000 cP as hydrophilic polymer; 2 mg of magnesium stearate and 4 g of talc as lubricants. The tablets were coated in a traditional dragée kettle with an ammonium methacrylate copolymer film containing the following ingredients. ("AM copolymer" means ammonium methacrylate copolymer.)

| | Amount (g) | |
|---|---|---|
| Ingredients of the film | I | II |
| AM copolymer RL 30% | 125 | 41.6 |
| AM copolymer RS 30% | — | 83.4 |
| Triethyl citrate | 7 | 7 |
| Dimethylpolysiloxane of 35% | 4 | 4 |

The coating of the tablets was carried out until a cover of 7 mg/cm$^2$ was achieved, which means 14.3 mg of coat weight on each tablet. On a part of the coated tablets a hole of 0.5 mm diameter was bored, thereafter the rate of active agent release was determined both for the unbored as well as bored-out tablets by using a paddle-mixer dissolution-investigating equipment at a rate of stirring with 100 revolutions/minute; and 900 ml of 0.1N hydrochloric acid.

The following measurement results were obtained:

| | Sign of the coat | | | |
|---|---|---|---|---|
| | I | | II | |
| Time of dissolution hours | Unbored % by weight | Bored % by weight | Unbored % by weight | Bored % by weight |
| 1 hour | 40.4 | 42.2 | 11.4 | 15.1 |
| 2 hours | 54.7 | 66.5 | 20.3 | 26.0 |
| 3 hours | 76.4 | 96.2 | 32.5 | 45.2 |
| 4 hours | 80.1 | 100.0 | 47.1 | 78.6 |
| 5 hours | 95.1 | 100.0 | 58.0 | 87.9 |
| 6 hours | 99.9 | 100.0 | 66.9 | 95.9 |

The following conclusions could be drawn from the experimental results:

In the case of the easily permeable AM copolymer RL coat, water diffuses in through the coat to the tablet interior and dissolves salbutamol. The release of salbutamol proceeds partly by diffusion through the coat (see the dissolution data of unbored tablets), partly on effect of the osmotic pressure developing in the tablet by pressing out through the bore.

The permeability of the coat can be controlled by mixing the AM copolymer RL with AM copolymer RS, however, the film prepared in this manner is not semipermeable since it is permeable also to the active agent in addition to water. An amount of 66% of salbutamol is released by diffusion within 6 hours; whereas additionally about 30% of the active agent are pressed out through the opening bored on the coat under effect of the osmotic pressure.

Figure 1:
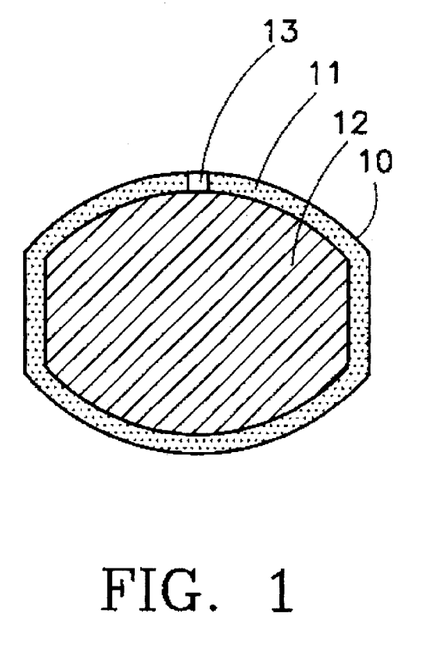
Figure 2:
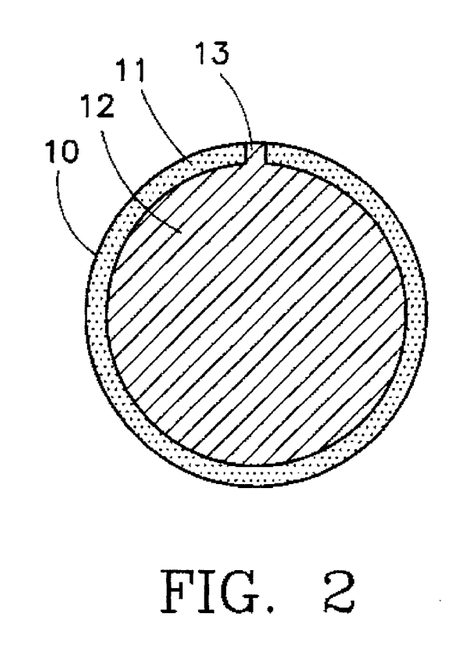
Figure 3:
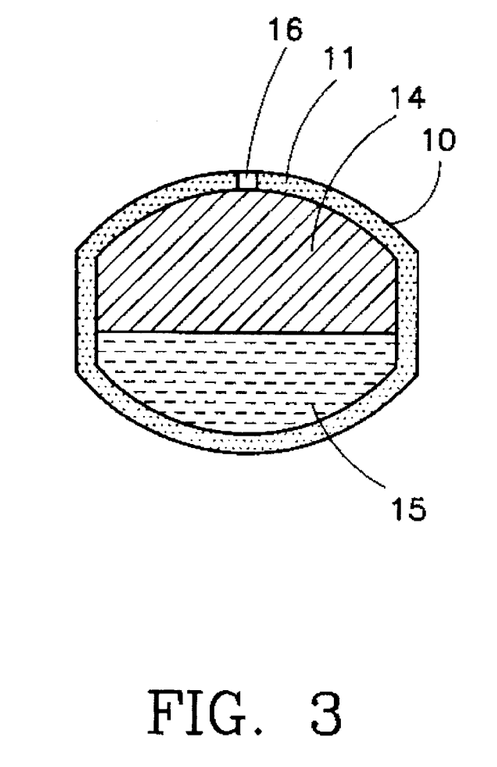
FIGS. 3–6 show the structures of the tablets.
Figure 4:
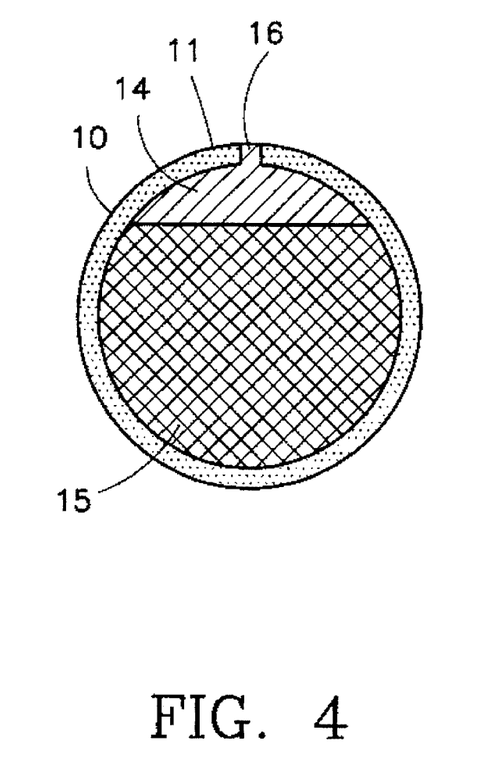
Figure 5:
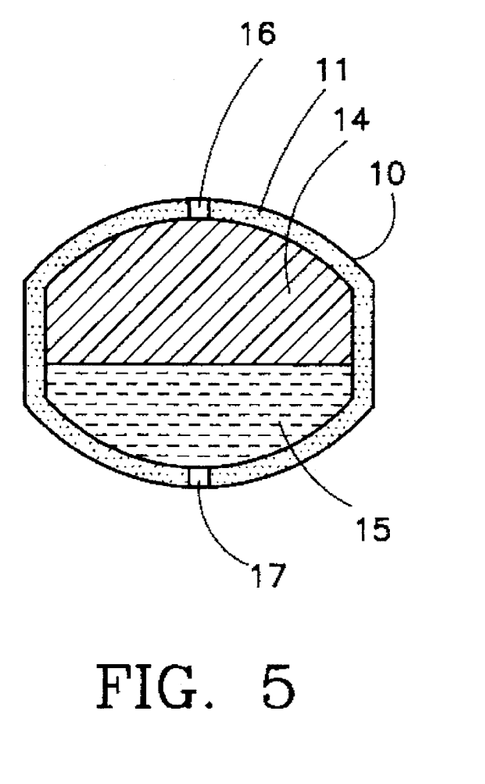
Figure 6:
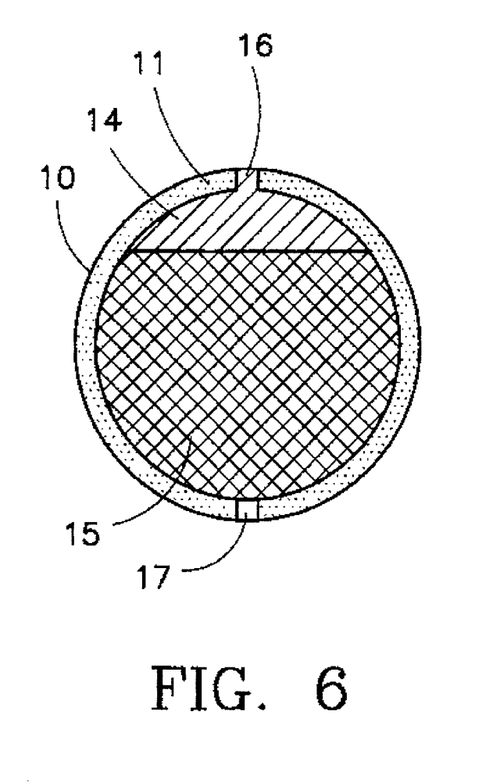
Figure 7:
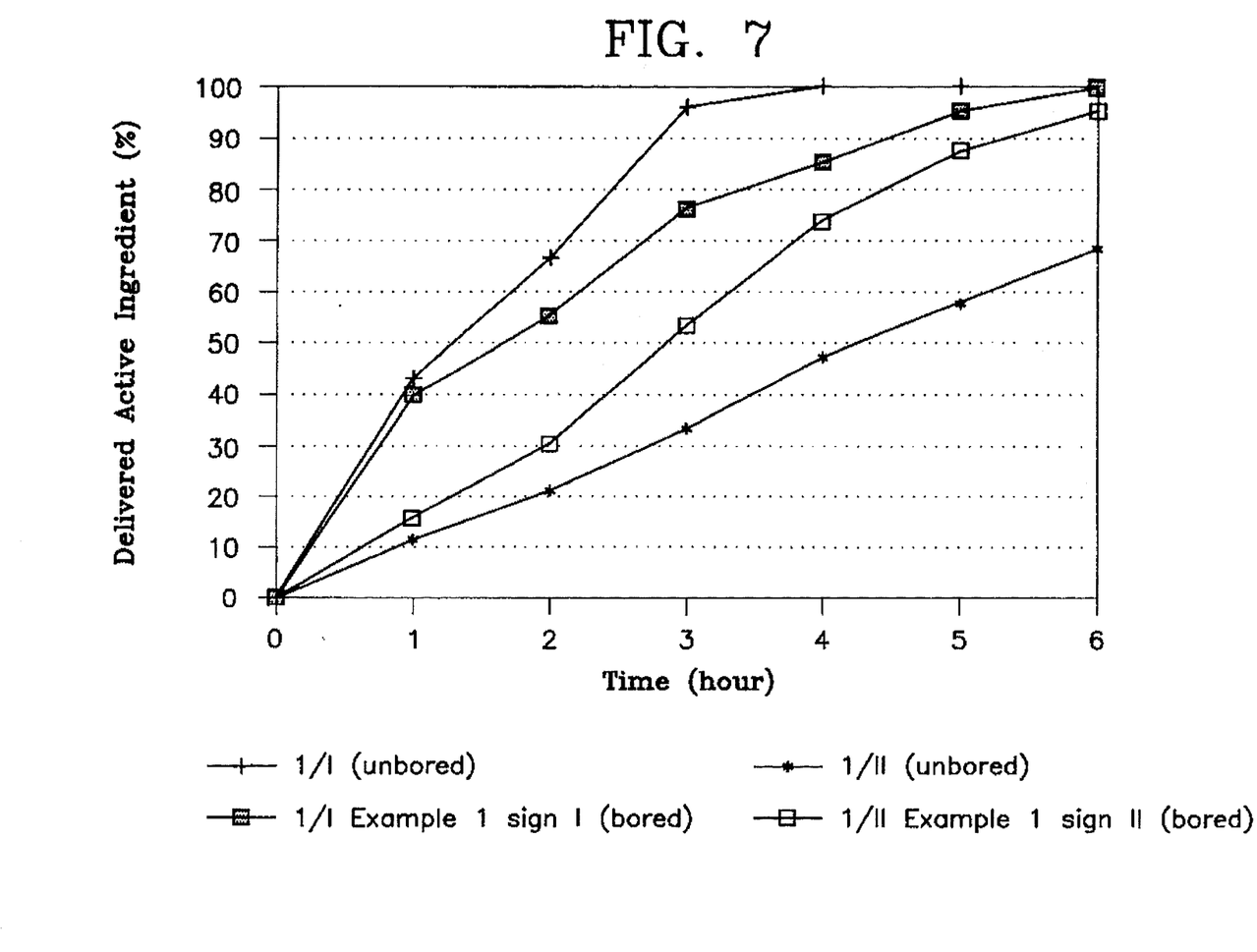
FIGS. 7–9 are graphic illustrations for dissolution and drug release.

The data of dissolution are graphically illustrated in FIG. 7.

Example 2

Example for comparison

The tablets according to Example 1 weighing 200 mg each and containing 8 mg of salbutamol base each as active agent were prepared by omitting the hydrophilic polymer, i.e. 20 mg of HPMC from the composition and substituting additional 20 mg of lactose monohydrate therefor. The tablets were similarly provided with 7 mg/cm² amount of coat signed as II according to Example 1. Then, after boring a hole of 0.5 mm in diameter on a part of the tablets, the drug-release of unbored and bored tablets were measured.

According to these examinations, 6% of the active agent were released from the unbored tablets whereas the release was 8% of active agent from the bored tablets during 6 hours in opposition to the measured value of 67% or 96%, respectively, by using coat II of Example 1. Thus, it has been proven by this Example that neither diffusive nor osmotic drug-release occur without the use of HPMC as hydrophilic polymer swelling on effect of water.

Example 3

Round, biconvex-shaped tablets of 9 mm in diameter were prepared which contained 30 mg of nifepidine (chemically 1,4-dihydro-2,6-dimethyl-4-(2-nitrophenyl)-3,5-pyridinedicarboxylic acid dimethyl ester) as active agent; 211 mg of lactose monohydrate as filling material; 30 mg of HPMC of 2208 type in a 2% aqueous solution with a viscosity of 15000 cP as hydrophilic polymer; 1 mg of colloidal silicon dioxide, 2 mg of magnesium stearate and 6 mg of talc as lubricants. The tablets were coated by using the following aqueous coating dispersion:

|  | Parts by weight |
| --- | --- |
| AM copolymer RL 30% | 140.0 |
| Triethyl citrate | 8.0 |
| Dimethylpolysiloxane emulsion of 35% | 4.5 |

An amount of 22.3 mg of film-coat were applied onto the tablets which corresponds to 7 mg/cm² of coating material, then a hole of 0.5 mm in size was bored on the coat.

The drug-release of the tablets was determined by using 0.1N hydrochloric acid as medium at 37° C. temperature in a paddle-mixer of 2-type according to USP, at a rate of stirring with 100 revolutions/minute. The amount of active agent released from the tablets as a function of the duration of dissolution was as follows:

| Hours | amount % |
| --- | --- |
| 1 | less than 1 |
| 3 | 5.4 |
| 5 | 25 |
| 8 | 39.5 |
| 10 | 48.3 |
| 24 | 80 |

Figure 8:
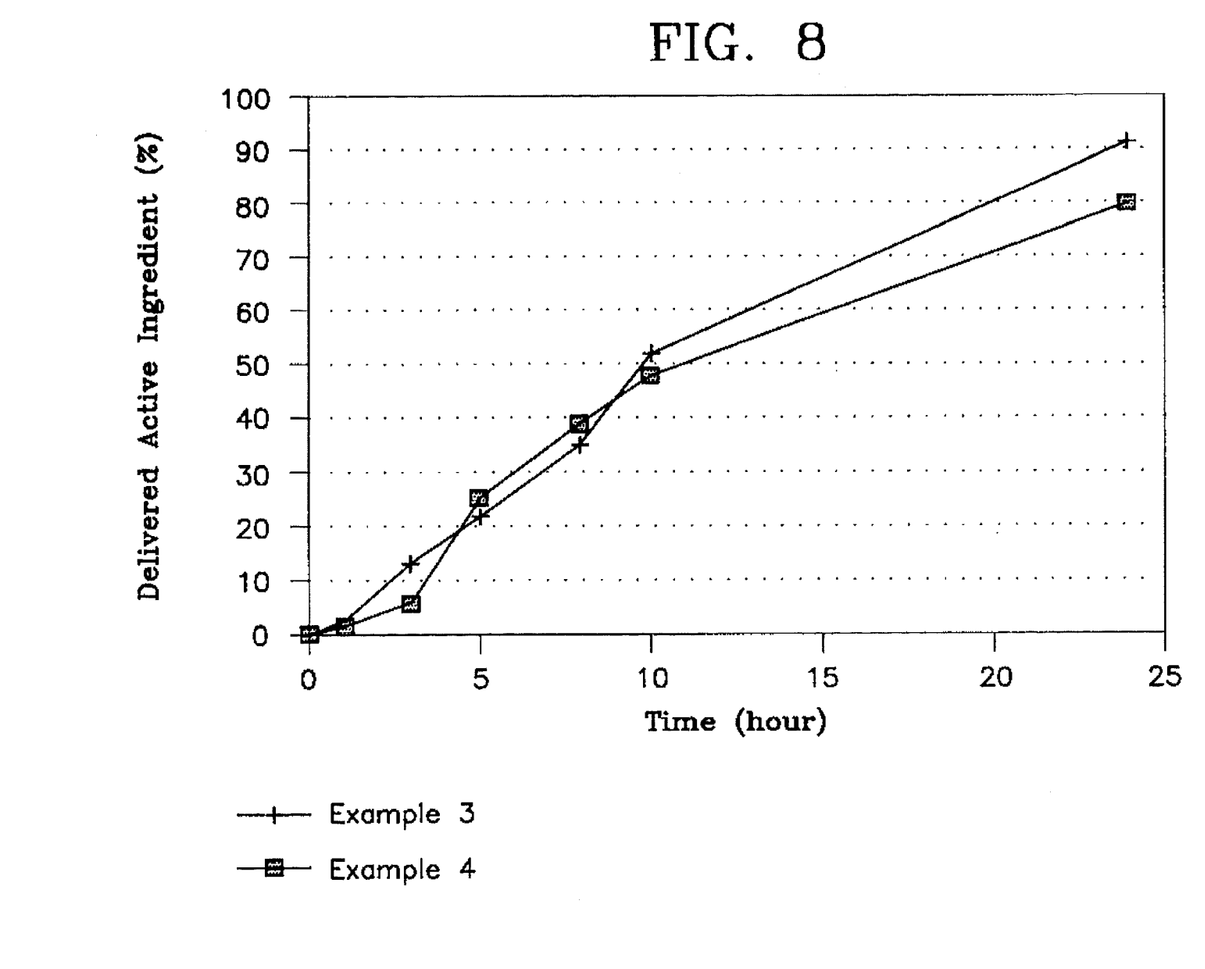

The data of dissolution are graphically illustrated in FIG. 8.

Example 4

Two-layer, round, biconvex-shaped tablets of 8 mm in size were prepared, one layer of which contained 30 mg of nifedipine as active agent; 142 mg of lactose monohydrate as filling material; 8 mg of hydroxypropyl-cellulose as binding material; 20 mg of 2208 type HPMC having 4000 cP viscosity in 2% aqueous solution as hydrophilic polymer; 1 mg of colloidal silicon dioxide, 2 mg of magnesium stearate and 5 mg of talc as lubricants; whereas the other layer of the tablet contained 42 mg of HPMC being identical with the above-used material, i.e. 2208 type HPMC having 4000 cP viscosity in 2% aqueous solution. The tablets were coated by using the following coating suspension. ("AM copolymer" means ammonium methacrylate copolymer.)

| Ingredients of the coating suspension | Parts by weight |
| --- | --- |
| AM copolymer RL 30% | 42 |
| AM copolymer RS 30% | 84 |
| Triethyl citrate | 7 |
| Dimethylpolysiloxane emulsion of 35% | 3 |

The coating of tablets was carried out until a coat weight of 28 mg/tablet (9.8 mg/cm²) was achieved. Thereafter, a hole of 0.5 mm diameter was bored on the yellow part containing the active agent of the tablets.

The drug-release of the tablets was measured by using the method described in Example 3. The results of these measurements are illustrated in FIG. 8.

The quantitative data are as follows:

| Hours | Amount % |
| --- | --- |
| 1 | less than 1 |
| 3 | 12 |
| 5 | 22 |
| 8 | 36 |
| 12 | 54 |
| 24 | 92 |

Example 5

A two-layer tablet according to Example 4 was prepared in such a manner that the ingredients of the layer containing the active agent were completely identical whereas the layer containing no active agent contained: 25 mg of 2906 type hydroxypropyl-methylcellulose having 4000 cP viscosity in 2% aqueous solution as hydrophilic polymer; 25 mg of microcrystalline cellulose as water-insoluble filling material; 1.8 mg of polyoxyethylene glycol 6000 as binding material; and 0.2 mg of magnesium stearate as lubricant. Subsequently, the two-layer tablets were coated until a coat weight of 4 mg was achieved by using an aqueous solution of 2910 type hydroxypropyl-methylcellulose having 6 cP viscosity in 2% aqueous solution and then an additional coat weight of 28 mg (9.8 mg/cm²) was achieved by using a coating dispersion of the following ingredients. ("AM copolymer" means ammonium methacrylate copolymer.) The amount of this intermediate coat of hydroxypropylmethyl cellulose amounts to about 1–5 mg/cm².

| Ingredients of the coating dispersion | Parts by weight |
| --- | --- |
| AM copolymer RL 30% | 105 |
| AM copolymer RS 30% | 105 |
| Triethyl citrate | 12 |
| Dimethylpolysiloxane emulsion of 35% | 6.7 |
| Water filled up to | 350 |

Figure 9:
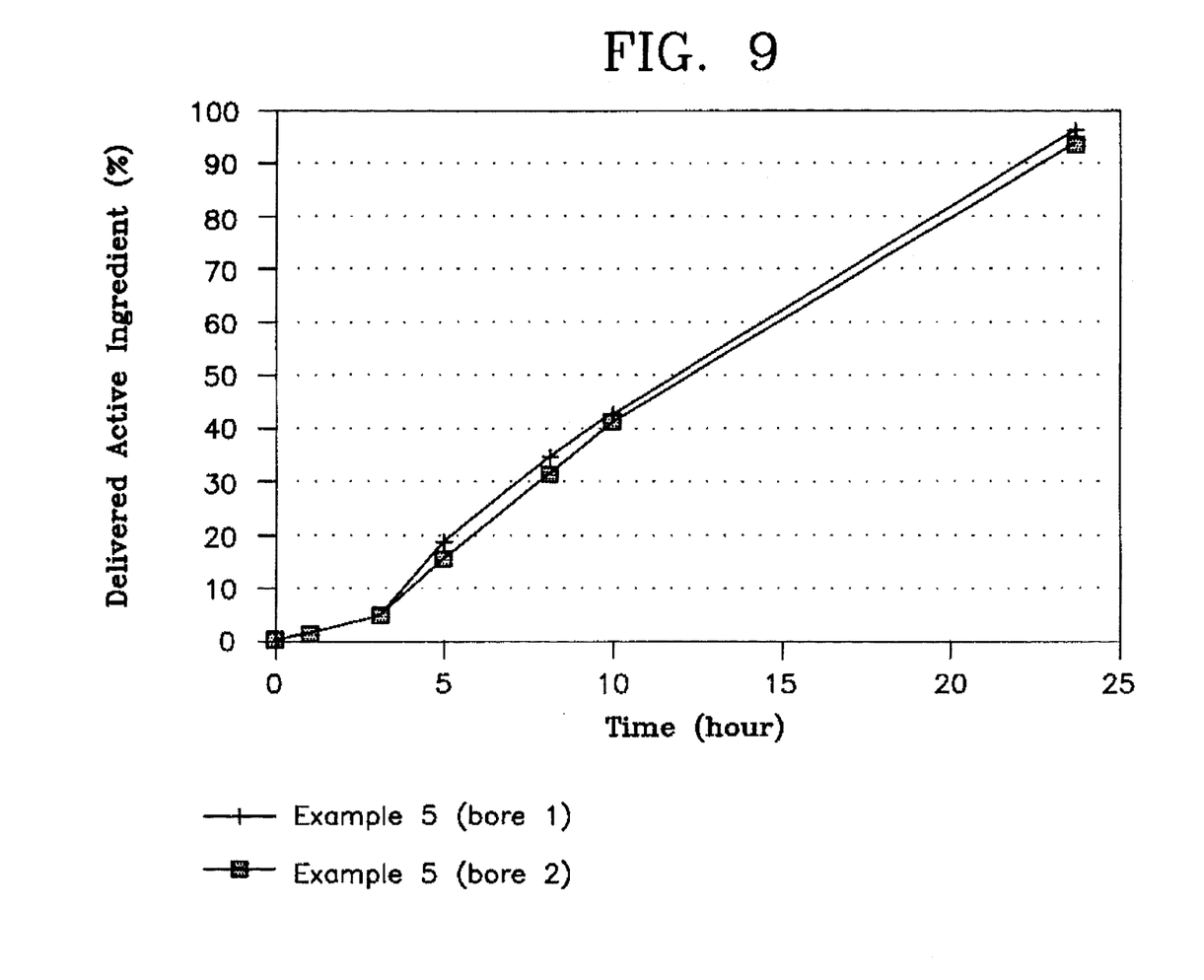

In one part of the tablets one hole of 0.3 mm in diameter was bored on the tablet side containing the active ingredient; and two holes were bored on both sides of another part of the tablets. The drug-release of the tablets was determined as described in Example 3. The experimental results are illustrated on the curves of FIG. 9.

Example 6

Two-layer tablets were prepared by producing tablets with double amount, i.e. 60 mg of active agent from the granulates described in Example 5. In this case the diameter of tablets was 10 mm whereas their weight was twice larger than that of the tablets according to Example 5, i.e. 520 mg. Then, the two-layer tablets were coated until a coat weight of 4 mg each was achieved by using an aqueous solution of 2910 type hydroxypropyl-methylcellulose having 6 cP viscosity in 2% aqueous solution and successively until an additional 28 mg of coat weight was achieved by using a coating dispersion of the following ingredients. ("AM copolymer" means ammonium methacrylate copolymer.)

| Ingredients of the coating dispersion | Parts by weight |
| --- | --- |
| AM copolymer RL 30% | 105 |
| AM copolymer RS 30% | 105 |
| Triethyl citrate | 12 |
| Dimethylpolysiloxane emulsion of 35% | 6.7 |
| Water filled up to | 350 |

One hole of 0.3 mm in diameter each was bored on the side containing the active ingredient of one part of the tablets; and two holes were bored on both sides of another part of the tablets. The drug-release of the tablets was determined as described in Example 3. The following dissolution data were obtained:

| Hours | Amount % |
| --- | --- |
| 3 | 1.7 |
| 5 | 12.4 |
| 8 | 20.7 |
| 24 | 94.9 |

We claim:

1. A diffusion-osmotic controlled drug-release pharmaceutical composition comprising a tablet core containing a therapeutically active agent and a hydrophilic polymer, wherein said tablet core is coated with a polymeric film-coat, and said film-coat contains at least one bore in said film-coat in contact with said tablet core, said film-coat comprising an ammonium methacrylate copolymer and said hydrophilic polymer comprising hydroxypropyl methylcellulose, said film-coat being present in an amount of 3 to 25 mg/cm$^2$ in relation to the surface of said tablet core.

2. The composition according to claim 1, wherein said hydroxypropyl methylcellulose is present in an amount of 5 to 30% by weight in relation to the weight of said tablet core.

3. The composition according to claim 1, said tablet core further comprising 0 to 90% by weight of filling material, 0 to 5% by weight of binding material, and 0 to 5% by weight of lubricant in relation to the weight of said tablet core.

4. The composition according to claim 3, wherein said filling material is cellulose, microcrystalline cellulose, starch, lactose, mannitol, or secondary calcium phosphate.

5. The composition according to claim 3, wherein said binding material is hydroxypropyl-cellulose, methylcellulose, hydroxypropylmethylcellulose, polyvinylpyrrolidone, ethylcellulose, gelatine, water-soluble starch, polyvinylalcohol, polyoxyethyleneglycol, or polyvinylbutyral.

6. The composition according to claim 3, wherein said lubricant is magnesium stearate, talc, stearic acid, hydrogenated castor oil, or colloidal silicon dioxide.

7. The composition according to claim 1, wherein said ammonium methacrylate copolymer has a relative molecular weight of 100,000 to 200,000 and contains 1 molar part of ethyl acrylate, 2 molar parts of methyl methacrylate and 0.1 to 0.2 molar part of (trimethylammonio)-ethyl methacrylate.

8. The composition according to claim 1, wherein said ammonium methacrylate copolymer comprises a 1:10 to 10:1 ratio of an ammonium methacrylate copolymer with a relative molecular weight of 150,000 containing 1 molar part of ethyl acrylate, 2 molar parts of methyl methacrylate and 0.1 molar part of (trimethylammonio)-ethyl methacrylate to an ammonium methacrylate copolymer with a relative molecular weight of 150,000 containing 2 molar parts of methyl methacrylate, 1 molar part of ethyl methacrylate and 0.2 molar part of (trimethylammonio)-ethyl methacrylate.

9. The composition according to claim 1, wherein said hydroxypropyl methylcellulose contains 20 to 30% by weight of methoxy groups and 5 to 12% by weight of hydroxypropyl groups and has a viscosity of 3 to 100,000 cP in a 2% aqueous solution.

10. A diffusion-osmotic controlled drug-release pharmaceutical composition comprising a tablet core containing a therapeutically active agent, 5 to 30% by weight of hydroxypropyl methylcellulose, 0 to 90% by weight of filling material, at most 5% by weight of binding material and at most 5% by weight of lubricant in relation to the total weight of said tablet core; wherein said tablet core is coated with a polymeric film-coat of an ammonium methacrylate copolymer, and said film-coat contains at least one bore in said film-coat in contact with said tablet core, said film-coat being present in amount of 3 to 25 mg/cm$^2$ in relation to the surface of said tablet core, and said film-coat contains one or more bores of 0.1 to 1.0 mm$^2$ in cross-section.

11. A diffusion-osmotic controlled drug-release pharmaceutical composition comprising a two-layer tablet core, wherein the first layer of said two-layer tablet core contains a therapeutically active agent and a hydrophilic polymer, and the second layer of said two-layer tablet core contains a hydrophilic polymer, said two-layer tablet core being covered with a polymeric film-coat, the part of said film-coat in contact with said first layer contains at least one bore and the part of said film-coat in contact with said second layer optionally contains at least one bore, said film-coat comprising an ammonium methacrylate copolymer and said hydrophilic polymer comprising hydroxypropyl methylcellulose, said film-coat being present in an amount of 3 to 25 mg/cm$^2$ in relation to the surface of said two-layer tablet core.

12. The composition according to claim 11, wherein said hydroxypropyl methylcellulose in said first layer is present in an amount of 5 to 30% by weight in relation to the weight of said first layer.

13. The composition according to claim 11, wherein said hydroxypropyl methylcellulose in said second layer is present in an amount of 30 to 100% by weight in relation to the weight of said second layer.

14. The composition according to claim 11, wherein said first layer further comprises 0 to 90% by weight of filling material, 0 to 5% by weight of binding material, and 0 to 5% by weight of lubricant in relation to the weight of said first layer.

15. The composition according to claim 11, said second layer further comprising 0 to 70% by weight of filling material, 0 to 5% by weight of binding material, and 0 to 5% by weight of lubricant in relation to the weight of said second layer.

16. The composition according to claim 14, wherein said filling material is cellulose, microcrystalline cellulose, starch, lactose, mannitol, or secondary calcium phosphate.

17. The composition according to claim 14, wherein said binding material is hydroxypropyl-cellulose, methylcellulose, hydroxypropylmethylcellulose, polyvinylpyrrolidone, ethylcellulose, gelatine, water-soluble starch, polyvinylalcohol, polyoxyethyleneglycol, or polyvinylbutyral.

18. The composition according to claim 14, wherein said lubricant is magnesium stearate, talc, stearic acid, hydrogenated castor oil, or colloidal silicon dioxide.

19. The composition according to claim 15, wherein said filling material is cellulose, microcrystalline cellulose, starch, lactose, mannitol, or secondary calcium phosphate.

20. The composition according to claim 15, wherein said binding material is hydroxypropyl-cellulose, methylcellulose, hydroxypropylmethylcellulose, polyvinylpyrrolidone, ethylcellulose, gelatine, water-soluble starch, polyvinylalcohol, polyoxyethyleneglycol, or polyvinylbutyral.

21. The composition according to claim 15, wherein said lubricant is magnesium stearate, talc, stearic acid, hydrogenated castor oil, or colloidal silicon dioxide.

22. The composition according to claim 11, wherein said ammonium methacrylate copolymer has a relative molecular weight of 100,000 to 200,000 and contains 1 molar part of ethyl acrylate, 2 molar parts of methyl methacrylate and 0.1 to 0.2 molar part of (trimethylammonio)-ethyl methacrylate.

23. The composition according to claim 11, wherein said ammonium methacrylate copolymer comprises a 1:10 to 10:1 ratio of an ammonium methacrylate copolymer with a relative molecular weight of 150,000 containing 1 molar part of ethyl acrylate, 2 molar parts of methyl methacrylate and 0.1 molar part of (trimethylammonio)-ethyl methacrylate to an ammonium methacrylate copolymer with a relative molecular weight of 150,000 containing 2 molar parts of methyl methacrylate, 1 molar part of ethyl methacrylate and 0.2 molar part of (trimethylammonio)-ethyl methacrylate.

24. The composition according to claim 11, wherein said hydroxypropyl methylcellulose contains 20 to 30% by weight of methoxy groups and 5 to 12% by weight of hydroxypropyl groups and has a viscosity of 3 to 100,000 cP in a 2% aqueous solution.

25. The composition according to claim 11, wherein said hydroxypropyl methylcellulose in said second layer has a viscosity higher than 1000 cP in a 2% aqueous solution.

26. A diffusion-osmotic controlled drug-release pharmaceutical composition comprising a two-layer tablet core, wherein the first layer of said two-layer tablet core contains a therapeutically active agent, 5 to 30% by weight of hydroxypropyl methylcellulose, 0 to 90% by weight of filling material, at most 5% by weight of binding material and at most 5% by weight of lubricant in relation to the total weight of said first layer; and the second layer of said two-layer tablet core contains 30 to 100% by weight of hydroxypropyl methylcellulose having a viscosity higher than 1000 cP in 2% aqueous solution, 0 to 70% by weight of filling material, 0 to 5% by weight of binding material and 0 to 5% by weight of lubricant in relation to the total weight of said second layer; said two-layer tablet core being covered with a polymeric film-coat containing an ammonium methacrylate copolymer, the part of said film-coat in contact with said first layer contains at least one bore and the part of said film-coat in contact with said second layer optionally contains at least one bore, said film-coat being present in amount of 3 to 25 mg/cm$^2$ in relation to the surface of said two-layer tablet core.

27. A process for the preparation of a diffusion-osmotic controlled drug-release pharmaceutical composition comprising a tablet core containing a therapeutically active agent and a hydrophilic polymer, and said tablet core is coated with a polymeric film-coat, wherein said film-coat contains at least one bore in said film-coat in contact with said tablet core; said process comprising using hydroxypropyl methylcellulose as said hydrophilic polymer and an ammonium methacrylate copolymer as said coating material in an amount of 3 to 25 mg/cm$^2$ in relation to the surface of said tablet core.

28. The process according to claim 27, comprising using 5 to 30% by weight of said hydroxypropyl methylcellulose in relation to the weight of said tablet core.

29. The process according to claim 27, comprising using in said tablet core 0 to 90% by weight of filling material, 0 to 5% by weight of binding material, and 0 to 5% by weight of lubricant in relation to the weight of said tablet core.

30. The process according to claim 29, wherein said filling material is cellulose, microcrystalline cellulose, starch, lactose, mannitol, or secondary calcium phosphate.

31. The process according to claim 29, wherein said binding material is hydroxypropyl-cellulose, methylcellulose, hydroxypropylmethylcellulose, polyvinylpyrrolidone, ethylcellulose, gelatine, water-soluble starch, polyvinylalcohol, polyoxyethyleneglycol, or polyvinylbutyral.

32. The process according to claim 29, wherein said lubricant is magnesium stearate, talc, stearic acid, hydrogenated castor oil, or colloidal silicon dioxide.

33. The process according to claim 27, wherein said ammonium methacrylate copolymer has a relative molecular weight of 100,000 to 200,000 and contains 1 molar part of ethyl acrylate, 2 molar parts of methyl methacrylate and 0.1 to 0.2 molar part of (trimethylammonio)-ethyl methacrylate.

34. The process according to claim 27, wherein said ammonium methacrylate copolymer comprises a 1:10 to 10:1 ratio of an ammonium methacrylate copolymer with a relative molecular weight of 150,000 containing 1 molar part of ethyl acrylate, 2 molar parts of methyl methacrylate and 0.1 molar part of (trimethylammonio)-ethyl methacrylate to an ammonium methacrylate copolymer with a relative molecular weight of 150,000 containing 2 molar parts of methyl methacrylate, 1 molar part of ethyl methacrylate and 0.2 molar part of (trimethylammonio)-ethyl methacrylate.

35. The process according to claim 27, wherein said hydroxypropyl methylcellulose contains 20 to 30% by weight of methoxy groups and 5 to 12% by weight of hydroxypropyl groups and has a viscosity of 3 to 100,000 cP in a 2% aqueous solution.

36. A process for the preparation of a diffusion-osmotic controlled drug-release pharmaceutical composition comprising a tablet core containing a therapeutically active agent and hydroxypropyl methylcellulose, wherein said tablet core is coated with a polymeric film-coat of an ammonium methacrylate copolymer, and said film-coat contains at least one bore in said film-coat in contact with said tablet core; said process comprising mixing a therapeutically active agent with 5 to 30% by weight of hydroxypropyl methylcellulose and 0 to 90% by weight of filling material in relation to the total weight of said tablet core to form a mixture; mixing at most 5% by weight of lubricant with said mixture directly or after granulating with at most 5% by weight of binding material; preparing said tablet core by compression; coating said tablet core with an ammonium methacrylate copolymer in an amount of 3 to 25 mg/cm$^2$ in relation to the surface of said tablet core to form a film-coat on said tablet core; and establishing at least one bore of 0.01 to 1.0 mm$^2$ in cross-section on said film-coat.

37. The process according to claim 36, wherein said ammonium methacrylate copolymer is in an aqueous dispersion or solution with ethanol, isopropanol, acetone or mixtures thereof.

38. A process for the preparation of a diffusion-osmotic controlled drug-release pharmaceutical composition comprising a two-layer tablet core, wherein the first layer of said two-layer tablet core contains a therapeutically active agent and a hydrophilic polymer, wherein the second layer of said two-layer tablet core contains a hydrophilic polymer, wherein said two-layer tablet core is covered with a polymeric film-coat of an ammonium methacrylate copolymer, the part of said film-coat in contact with said first layer contains at least one bore and the part of said film-coat in contact with said second layer optionally contains at least one bore; said process comprising using hydroxypropyl methylcellulose as said hydrophilic polymer and an ammonium methacrylate copolymer as said coating material in an amount of 3 to 25 mg/cm$^2$ in relation to the surface of said two-layer tablet core.

39. The process according to claim 38, comprising using in said first layer 5 to 30% by weight of said hydroxypropyl methylcellulose in relation to the weight of said first layer.

40. The process according to claim 38, comprising using in said second layer 30 to 100% by weight of said hydroxypropyl methylcellulose in relation to the weight of said second layer.

41. The process according to claim 38, comprising using in said first layer 0 to 90% by weight of filling material, 0 to 5% by weight of binding material, and 0 to 5% by weight of lubricant in relation to the weight of said first layer.

42. The process according to claim 38, comprising using in said second layer 0 to 70% by weight of filling material, 0 to 5% by weight of binding material, and 0 to 5% by weight of lubricant in relation to the weight of said second layer.

43. The process according to claim 41, wherein said filling material is cellulose, microcrystalline cellulose, starch, lactose, mannitol, or secondary calcium phosphate.

44. The process according to claim 41, wherein said binding material is hydroxypropyl-cellulose, methylcellulose, hydroxypropylmethylcellulose, polyvinylpyrrolidone, ethylcellulose, gelatine, water-soluble starch, polyvinylalcohol, polyoxyethyleneglycol, or polyvinylbutyral.

45. The process according to claim 41, wherein said lubricant is magnesium stearate, talc, stearic acid, hydrogenated castor oil, or colloidal silicon dioxide.

46. The process according to claim 38, wherein said ammonium methacrylate copolymer has a relative molecular weight of 100,000 to 200,000 and contains 1 molar part of ethyl acrylate, 2 molar parts of methyl methacrylate and 0.1 to 0.2 molar part of (trimethylammonio)-ethyl methacrylate.

47. The process according to claim 38, wherein said ammonium methacrylate copolymer comprises a 1:10 to 10:1 ratio of an ammonium methacrylate copolymer with a relative molecular weight of 150,000 containing 1 molar part of ethyl acrylate, 2 molar parts of methyl methacrylate and 0.1 molar part of (trimethylammonio)-ethyl methacrylate to an ammonium methacrylate copolymer with a relative molecular weight of 150,000 containing 2 molar parts of methyl methacrylate, 1 molar part of ethyl acrylate and 0.2 molar part of (trimethylammonio)-ethyl methacrylate.

48. The process according to claim 38, wherein said hydroxypropyl methylcellulose contains 20 to 30% by weight of methoxy groups and 5 to 12% by weight of hydroxypropyl groups and has a viscosity of 3 to 100,000 cP in a 2% aqueous solution.

49. The process according to claim 38, wherein said hydroxypropyl methylcellulose in said second layer has a viscosity higher than 1000 cP in a 2% aqueous solution.

50. A process for the preparation of a diffusion-osmotic controlled drug-release pharmaceutical composition comprising a two-layer tablet core, wherein the first layer of said two-layer tablet core contains a therapeutically active agent and hydroxypropyl methylcellulose, wherein the second layer of said two-layer tablet core contains hydroxypropyl methylcellulose, wherein said two-layer tablet core is covered with a polymeric film-coat of an ammonium methacrylate copolymer, the part of said film-coat in contact with said first layer contains at least one bore and the part of said film-coat in contact with said second layer optionally contains at least one bore; said process comprising mixing a therapeutically active agent with 5 to 30% by weight of hydroxypropyl methylcellulose and 0 to 90% by weight of filling material in relation to the total weight of said first layer to form a mixture; mixing at most 5% by weight of lubricant with said mixture directly or after granulating with at most 5% by weight of binding material; preparing said first layer by compression; preparing a two-layer tablet core by pressing onto said first layer said second layer (i) consisting of hydroxypropyl methylcellulose having a viscosity higher than 1000 cP in 2% aqueous solution or (ii) containing 30 to 100% by weight of hydroxypropyl methylcellulose having a viscosity higher than 1000 cP in 2% aqueous solution, 0 to 70% by weight of filling material, 0 to 5% by weight of binding material and 0 to 5% by weight of lubricant in relation to the total weight of said second layer; coating said two-layer tablet core with an ammonium methacrylate copolymer in an amount of 3 to 25 mg/cm$^2$ in relation to the surface of said two-layer tablet core to form a film-coat on said two-layer tablet core; and establishing at least one bore on said film-coat in contact with said first layer and optionally at least one bore on said film-coat in contact with said second layer.

51. The process according to claim 50, wherein said ammonium methacrylate copolymer is in an aqueous dispersion or solution with ethanol, isopropanol, acetone or mixtures thereof.

\* \* \* \* \*